United States Patent [19]

Klenk et al.

[11] 4,360,682
[45] Nov. 23, 1982

[54] STABILIZING CAPROLACTONES WITH DIHYDROXYBENZENES

[75] Inventors: Herbert Klenk; Rolf Wirthwein, both of Hanau; Helmut Waldmann, Leverkusen; Hermann Seifert, Cologne, all of Fed. Rep. of Germany

[73] Assignees: Deutsche Gold- und Silberscheideanstalt vormals Roessler, Frankfurt am Main; Bayer Aktiengesellschaft, Leverkusen, both of Fed. Rep. of Germany

[21] Appl. No.: 148,869

[22] Filed: May 12, 1980

[30] Foreign Application Priority Data

May 23, 1979 [DE] Fed. Rep. of Germany ....... 2920847

[51] Int. Cl.³ .......................................... C07D 313/04
[52] U.S. Cl. ................... 549/266; 252/403; 252/404
[58] Field of Search ................. 260/343; 252/404, 403

[56] References Cited

U.S. PATENT DOCUMENTS

| | | | |
|---|---|---|---|
| 2,831,817 | 4/1958 | Ecke et al. | 252/404 |
| 3,227,730 | 1/1966 | Goldsmith et al. | 260/343 |
| 3,274,216 | 9/1966 | Goldsmith et al. | 260/343 |
| 3,426,051 | 2/1969 | Hoch | 252/404 |
| 3,953,531 | 4/1976 | Ohi | 252/404 |

FOREIGN PATENT DOCUMENTS 2160405 12/1971 Fed. Rep. of Germany .
2215909 10/1973 Fed. Rep. of Germany .

OTHER PUBLICATIONS

Hawley, The Condensed Chemical Dictionary 9th Edition p. 453.

*Primary Examiner*—Jane T. Fan
*Attorney, Agent, or Firm*—Sprung, Horn, Kramer & Woods

[57] ABSTRACT

Caprolactones such as ε-caprolactone are stabilized against discoloration with dihydroxybenzenes such as hydroquinone or compounds of the formula

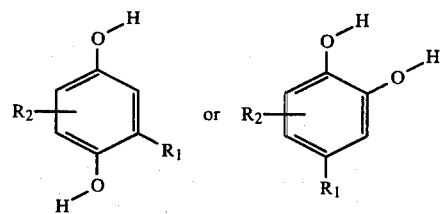

in which
$R_1$ is alkyl of 1 to 8 carbon atoms, and
$R_2$ is hydrogen or alkyl of 1 to 8 carbon atoms.

Even the presence of air is not detrimental.

9 Claims, No Drawings

STABILIZING CAPROLACTONES WITH DIHYDROXYBENZENES

The present invention relates to the prevention of undesired discoloration of caprolactones, preferably ε-caprolactone, and stabilization of these important industrial compounds is thereby achieved.

As is known, one of the main uses of caprolactones, especially ε-caprolactone, is the preparation of chemical intermediate products, such as, for example, polycaprolactone-polyols. Such polyols are the starting material in the preparation of polyurethanes, which are widely used. In many of these fields of application, such as, for example, polyurethane fibers and coatings, virtually colorless products are demanded by the consumer.

This presents great difficulties since, because of the known properties of caprolactones, above all ε-caprolactone, of discoloring after a relatively short storage time, the polyester-ols and polyurethanes prepared from such a caprolactone are likewise colored The production of caprolactones which are truly stable in color is thus of great industrial importance.

In order to avoid additional purification operations such as, for example, distillation or chemical treatment, especially in the case of fresh or aged ε-caprolactone, it has been the practice to use certain organic substances as stabilizers for caprolactones.

Thus, it is known, for example from U.S. Pat. No. 3,277,730, that triorgano-phosphites can be used as stabilizers for monomeric caprolactones. This patent specification also mentions phenols sterically hindered by tert.-butyl, and also monoalkyl ethers of hydroquinone, for example its monomethyl ether, as stabilizers for ε-caprolactone. However, according to the statements of U.S. Pat. No. 3,274,216, the stabilizing effect was inadequate and a mixture of triorgano-phosphites and alkylphenols was recommended in this patent. The stabilizing operations were carried out predominantly in an inert gas atmosphere consisting of very pure nitrogen. Air could indeed also be used, but was regarded as being less favorable.

According to German Offenlegungsschrift No. 2,160,405, such a mixture of alkylphenols and triorgano-phosphites or triorgano-phosphites by themselves have an adverse effect on the physical properties of the polyurethane product prepared therefrom, and so the addition of an inhibiting amount of triorgano-phosphine compounds or triorgano-phosphinite compounds was proposed.

Triphenylphosphine is also employed as a stabilizer (see German Auslegeschrift No. 2,215,909), and in this case the stabilizing operation is carried out in an inert gas atmosphere, such as methane, natural gas, a noble gas or nitrogen.

The stabilizers and stabilizer mixtures have hitherto preferably been used in amounts of 250–1,000 ppm.

The processes mentioned are thus characterized in that the stabilizing of ε-caprolactone is carried out predominantly in an inert gas atmosphere, since, as is known, it is not always a simple matter to exclude oxygen or air from vessels such as reactor components, stirred kettles, mixing tanks and storage and transportation containers. In particular, the emptying and re-closing of even relatively small units requires a considerable technical effort if this is to be effected in the complete absence of air.

It is thus of great industrial importance and the aim of the invention to carry out the stabilizing of caprolactones, above all ε-caprolactone, directly in air, without any impairment of the caprolactones.

It has now been found that such a stabilization can be achieved if dihydroxybenzenes are added to the caprolactones, above all ε-caprolactone, in the customary manner, preferably in the presence of air.

The compounds to be employed as the dihydroxybenzenes in accordance with the invention are, in addition to hydroquinone itself, also compounds of the following general formulae I and II:

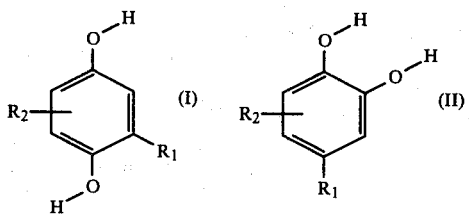

wherein
$R_1$ and $R_2$ can be identical or different and denote an alkyl group which has 1–8 carbon atoms, preferably an alkyl group which has 3–8 carbon atoms, and optionally is branched at the α-carbon atom, and
$R_2$ can also denote hydrogen.

Mixtures of such compounds can also be used.
The stabilizers are in general mixed with the caprolactones.

Those compounds in which $R_1$ is a tert.alkyl group, such as, for example, tert.-butyl, and $R_2$ is hydrogen, are preferred. Appropriate derivatives of catechols, for example 4-tert.-butyl-catechol, can thus be used.

The stabilizer is mixed with the caprolactone in customary apparatuses, such as, for example, mixing kettles.

The process is preferably carried out using freshly distilled caprolactone, and the stabilizer is in general used in amounts of 50–500 ppm, preferably in amounts of between 100 and 500 ppm.

The process according to the invention is illustrated by the following examples:

EXAMPLES

In all cases, 100 g of freshly distilled ε-caprolactone were introduced into a 250 ml glass beaker and the calculated amount of stabilizer was added. The open glass beaker was then placed in a warming cabinet, where it remained for 24 hours at a temperature of 100° C., and the color number of the ε-caprolactone was then determined in accordance with the ASTM method D 1209-54 (Pt-Co).

Table 1 shows the results obtained. Examples 1–5 are comparison examples carried out with stabilizers according to the state of the art.

Examples 6 and 7 illustrate the invention.

TABLE 1

| Sample No. | Stabilizer used | Amount | Color number of the caprolactone |
|---|---|---|---|
| 1 | no stabilizer | — | >>500 |
| 2 | 2,6-di-tert.-butylphenol | 100 ppm | ~500 |
| 3 | tributyl phosphite | 100 ppm | >500 |
| 4 | mixture of | | |

TABLE 1-continued

| Sample No. | Stabilizer used | Amount | Color number of the caprolactone |
|---|---|---|---|
| | (a) 2,6-di-tert.-butylphenol and | 50 ppm | 400 |
| | (b) tributyl phosphite | 50 ppm | |
| 5 | triphenylphosphine | 100 ppm | 500 |
| 6 | tert.-butyl hydroquinone | 100 ppm | 10–20 |
| 7 | 4-tert.-butylcatechol | 100 ppm | 10–20 |

The stabilizers mentioned, which are distinguished by the fact that they can be used in the presence of air, can, of course, also be used in a customary inert gas atmosphere.

It will be appreciated that the instant specification and examples are set forth by way of illustration and not limitation, and that various modifications and changes may be made without departing from the spirit and scope of the present invention.

What is claimed is:

1. A composition consisting essentially of caprolactone and a color stabilizing amount of a dihydroxybenzene of the formula

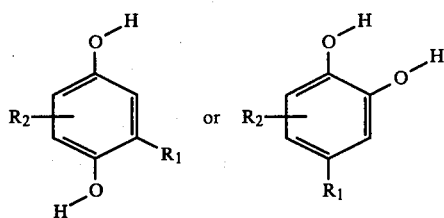

in which
R$_1$ is alkyl of 1 to 8 carbon atoms, and
R$_2$ is hydrogen.

2. A stabilized composition according to claim 1, wherein the dihydroxybenzene is present in about 50 to 500 ppm.

3. A stabilized composition according to claim 1, wherein the dihydroxybenzene is present in about 100 to 500 ppm.

4. A composition according to claim 1 wherein R$_1$ is alkyl of 1 to 8 carbon atoms branched at the alpha carbon atom.

5. A composition according to claim 1 wherein R$_1$ is a tert.-alkyl group.

6. A composition according to claim 1 wherein R$_1$ is an alkyl group of 3–8 carbon atoms.

7. A composition according to claim 1 wherein said caprolactone is stabilized with tertiary butyl hydroquinone.

8. A composition according to claim 1 wherein said caprolactone is stabilized with 4-tert.-butyl catechol.

9. A process for stabilizing caprolactone comprising adding thereto a color stabilizing effective amount of a composition consisting essentially of a dihydroxybenzene in the presence of air, said dihydroxybenzene being one of the formula

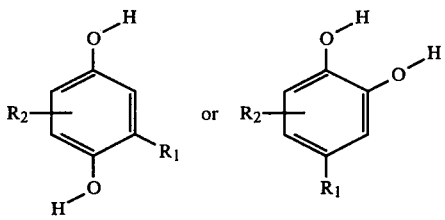

wherein
R$_1$ is alkyl of 1 to 8 carbon atoms, and
R$_2$ is hydrogen.

* * * * *